United States Patent
Koerdt et al.

(10) Patent No.: US 7,694,565 B2
(45) Date of Patent: Apr. 13, 2010

(54) ACOUSTIC METHOD FOR MEASURING A SIGNAL PROPAGATION TIME IN A MEDICAL LIQUID AND DEVICE FOR USING THIS METHOD

(75) Inventors: Franz-Wilhelm Koerdt, Bad Nauheim (DE); Peter Scheunert, Friedrichsdorf (DE); Dejan Nikolic, Frankfurt (DE); Klaus Metzner, Friedrichsdorf (DE); Alexander Kuhn, Lauterbach (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 727 days.

(21) Appl. No.: 10/568,830

(22) PCT Filed: Jul. 15, 2004

(86) PCT No.: PCT/EP2004/007812

§ 371 (c)(1),
(2), (4) Date: Nov. 6, 2006

(87) PCT Pub. No.: WO2005/029064

PCT Pub. Date: Mar. 31, 2005

(65) Prior Publication Data

US 2007/0186624 A1     Aug. 16, 2007

(30) Foreign Application Priority Data

Aug. 22, 2003  (DE) ................. 103 38 940

(51) Int. Cl.
*G01N 29/00*     (2006.01)
(52) U.S. Cl. .............. 73/597; 73/598; 73/602; 73/861.28
(58) Field of Classification Search ................ 73/53.01, 73/597, 602, 609, 617, 861.27, 861.28, 861.29, 73/598
See application file for complete search history.

(56) References Cited

U.S. PATENT DOCUMENTS 4,028,938 A    6/1977    Eck (Continued)

FOREIGN PATENT DOCUMENTS

DE    34 20 794 A1    12/1984

(Continued)

*Primary Examiner*—J M Saint Surin
(74) *Attorney, Agent, or Firm*—Jacobson Holman PLLC

(57) ABSTRACT

This invention relates to the field of signal transit time sensors, in particular sensors based on ultrasonic transit times. Existing electronic control circuits for such transit time sensors for measurements on medical liquids, in particular blood, are extremely complex or their time resolution is limited. However, the present invention makes use of a simple measurement technique which cannot be used directly at first for the time resolution to be achieved. In this method, an ordinary sampling method is used to detect the received signal (12). An oscillator-like received signal (12) generated by an emitted step-like signal is first sampled during a half-period (14, 15) and is checked with the help of a selection criterion. Only when the result of this check is positive is at least one interpolated or extrapolated contact point (20, 21) of the received signal (12) with a resting level (11) determined in a received signal-time diagram with the help of which the signal transit time or the change in signal transit time is determined.

18 Claims, 3 Drawing Sheets

U.S. PATENT DOCUMENTS

| | | | |
|---|---|---|---|
| 4,754,650 A | | 7/1988 | Smalling et al. |
| 5,123,286 A | | 6/1992 | Baumgärtner |
| 5,230,341 A | | 7/1993 | Polaschegg |
| 5,804,739 A | * | 9/1998 | Herrmann et al. ........ 73/861.18 |
| 6,212,936 B1 | | 4/2001 | Meisberger |
| 6,226,598 B1 | | 5/2001 | De Vanssay et al. |
| 6,295,873 B1 | * | 10/2001 | Condreva ..................... 73/597 |
| 6,527,728 B2 | | 3/2003 | Zhang |
| 6,542,761 B1 | | 4/2003 | Jahn et al. |
| 6,568,281 B1 | | 5/2003 | Sato et al. |
| 6,647,805 B2 | * | 11/2003 | Kobayashi et al. ....... 73/861.27 |
| 6,877,387 B1 | * | 4/2005 | Certon et al. ............ 73/861.29 |
| 7,073,395 B2 | * | 7/2006 | Suginouchi et al. ...... 73/861.27 |
| 7,207,939 B2 | * | 4/2007 | Husher ....................... 600/370 |
| 7,213,468 B2 | * | 5/2007 | Fujimoto ................. 73/861.27 |

FOREIGN PATENT DOCUMENTS

| | | |
|---|---|---|
| DE | 198 09 945 A1 | 9/1999 |
| DE | 100 51 943 A1 | 5/2002 |
| DE | 101 06 308 C1 | 7/2002 |
| EP | 0 855 577 A1 | 7/1998 |
| EP | 0 899 564 A2 | 3/1999 |
| EP | 0 902 883 | 3/1999 |
| EP | 0 943 369 A1 | 9/1999 |
| EP | 1 077 365 A2 | 2/2001 |
| WO | WO 97/46854 | 11/1997 |

\* cited by examiner

ACOUSTIC METHOD FOR MEASURING A SIGNAL PROPAGATION TIME IN A MEDICAL LIQUID AND DEVICE FOR USING THIS METHOD

CROSS-REFERENCE TO RELATED APPLICATION

This is a nationalization of PCT/EP2004/007812 filed 15 Jul. 2004 and published in German.

BACKGROUND OF THE INVENTION

1. Field of Invention

This invention relates to the field of signal transit time sensors, in particular sensors based on ultrasonic transit times.

The rate of propagation of a signal within a medium depends on the composition of the medium. In this way, by measuring the rate of propagation, it is possible to draw a conclusion regarding the medium itself. The corresponding measurement methods are often based on the propagation of ultrasonic waves. The measurement object, which in the case of the fluid to be tested may be in the form of a fluid-carrying line, for example, is arranged inside a measurement zone, which separates an ultrasonic transmitter from an ultrasonic receiver. If the length of the measurement zone is known, then it is possible with the help of the signal transit time to determine the rate of propagation from the transmitter to the receiver. If only a relative change is of interest, then it is possible to deduce directly the relative change in the rate of propagation from the relative change in the signal transit time as long as the measurement zone does not change in an unknown manner.

The measurement zone may be divided into different regions. If a medium flows through a line, the measurement zone is composed of a first region, comprising the walls of the line, and a second region, through which the actual measurement medium passes. Then if the composition of the medium changes, the resulting change in the signal transit time can in general be attributed solely to the change in the signal transit time in the second region, because the signal transit time in the first region does not change given a suitable choice of walls. If the signal transit time in the first region is known through a knowledge of the material of which the wall is made and the dimensions thereof, it is also easy to determine the absolute signal transit time in the second region.

In a hemodialysis treatment, blood is removed continuously from a patient in an extracorporeal blood circulation, purified by a hemodialyzer and returned to the patient. As an artificial kidney treatment, simultaneous removal of the liquid that has not been separated is not necessary. In this case, a given quantity of liquid is usually withdrawn from the patient during the treatment. However, if the liquid is withdrawn too rapidly, there may be unwanted side effects such as hypotension or an excessive drop in blood pressure.

The reduction in blood volume caused by the removal of liquid leads to an increase in blood density, i.e., a decrease in the blood-water content, which is in general also manifested in an increase in hematocrit; therefore, monitoring of the extracorporeal blood with the help of an ultrasonic transit time sensor was proposed in U.S. Pat. No. 5,230,341. In German patent application DE 100 51 943 A1 the influence of blood density variations on pulse wave transit time measurements is treated, where in one embodiment ultrasonic transit time measurements are employed to determine the blood density.

2. Description of the Prior Art

Ultrasonic transit time measurements have been proposed in German patent application DE 198 09 945 A1 also for monitoring the composition of the dialysis liquid. The attenuation of ultrasonic signals is, as described for example in European patent application EP 0 899 564 A2, evaluated for the recognition of air bubbles during the infusion of liquids into a patient.

For control and analysis of such sensors, certain electronic circuits are used to ensure the required accuracy. An example of such a circuit is given in German Patent DE 34 20 794 C2.

U.S. Pat. No. 6,542,761 discloses a multifunctional ultrasonic transit time sensor for performing measurements on extracorporeal blood; with this sensor, an inexpensive disposable part may be used for the line that carries blood through the measurement zone.

In the field of sensors on natural gas pipelines European patent EP 0 902 883 B1 describes a method in which the zero crossings of a received sound signal are determined for propagation time measurements of a sound signal.

SUMMARY OF THE INVENTION

Existing electronic control circuits for transit time sensors in blood are extremely complex or have a limited time resolution. Therefore, the object of this invention is to provide a simple and less susceptible transit time measurement method for the application on medical liquids, in particular blood, combined at the same time with a high time resolution. This invention also has the object of providing a device for the use of this method.

According to the teaching of this invention, this object is achieved by a method of measuring a signal transit time or a change in signal transit time, this method having the features of claim 1 and by means of a device for applying the method having the features of claim 14. Advantageous embodiments of this invention are the object of the subclaims.

The inventive method makes use here of a simple measurement technique which cannot be used directly for the time resolution to be achieved. An ordinary sampling method is used for detecting the received signal. Since the measurement medium already acts like a low-pass filter at the time ranges of relevance here, namely in the nanosecond and subnanosecond range, and since the receiver has a resonant frequency design, therefore a step-like signal emitted causes an oscillator-like received signal. According to this invention, this received signal is sampled at least during a half-period and is checked with the help of a selection criterion. Only if this check has a positive outcome is at least one interpolated or extrapolated point of contact with the received signal and a resting level in a received signal-time diagram determined, and the signal transit time or at least the change in signal transit time is determined with the help of this diagram.

The selection criterion ensures reliable detection of a received signal as the response to an emitted signal. The following interpolation or extrapolation step results in a considerable increase in the time resolution.

Different conditions may be used as the selection criterion. The area enclosed between the resting level and the received signal during the half-period and/or the extreme values may be compared with comparative values. Here again, another following half-period can be analyzed accordingly. Finally, the first half-period need not be used for the analysis. Any half-period selected is adequate.

Finally, through appropriate manufacturing specifications, it is possible to predetermine the resonant frequency of the receiver with a high precision, so that the duration of the half-period can also be used as a selection criterion. However, it must be recalled here that because of superimposed effects, not all half-periods last for the same period of time. Instead, each half-period has its own precisely defined duration.

In an advantageous embodiment of this invention, the attenuation of the signal is determined from the received signal thus detected, so that the inventive device is also suitable for detecting inclusions in the medium, e.g., air bubbles in blood, which are associated with attenuation of the signal, in addition to detecting the composition of the medium.

Apart from the application of the invention for measurements of signal transit times in blood the invention may also be used for measurements of signal transit times in other medical liquids like for example dialysis liquid in the case of artificial kidney treatments or infusion liquids.

BRIEF DESCRIPTION OF THE DRAWINGS

Additional details and advantages of this invention will now be described in greater detail on the basis of an exemplary embodiment illustrated in the drawings, which show.

DETAILED DESCRIPTION OF THE PREFERRED EMBODIMENTS

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

Figure 1:
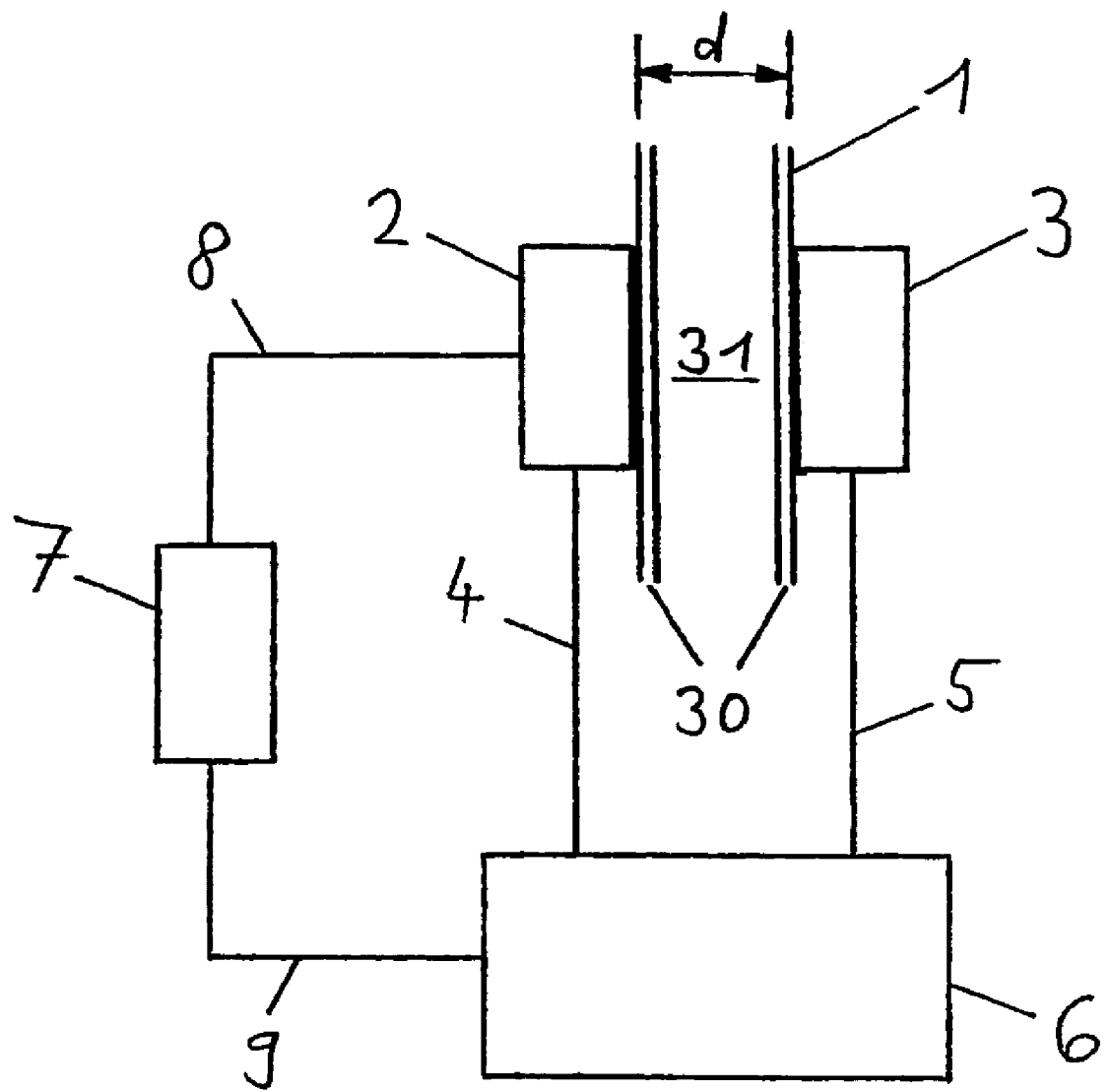
FIG. 1 a schematic diagram of an exemplary embodiment of the device according to this invention.

FIG. 1 shows an embodiment of the inventive device for use of the inventive method. A blood-carrying line 1 is situated between an ultrasonic transmitter 2 and an ultrasonic receiver 3 which are spaced a distance apart from one another by a measurement zone d. The measurement zone d is divided into two regions 30 and 31, the first region 30 including the walls of the line 1 and the second region 31 including the region through which blood flows. Line 1 may be, for example, a film-like disposable part such as that described in U.S. Pat. No. 6,542,761.

In addition, there is an analyzer unit 6, which is connected by a signal line 4 to the ultrasonic transmitter 2 and by a signal line 5 to the ultrasonic receiver 3. Analyzer unit 6 as well as the ultrasonic transmitter 2 are supplied with a system clock pulse over the system lines 8 and 9 by means of an oscillator 7.

The ultrasonic transmitter 2 sends step-like ultrasonic signals 10 (FIG. 2) as well as synchronized signals to the analyzer unit 6 over the signal line 4. An oscillator-like received signal 12, oscillating about a resting level 11, is received at the ultrasonic receiver 3 as a response to the step-like signal; this signal is also relayed to the analyzer unit 6 over the signal line 5. It is also possible to use the next ascending stage instead of the descending stage 10 for the method according to this invention.

Figure 2:
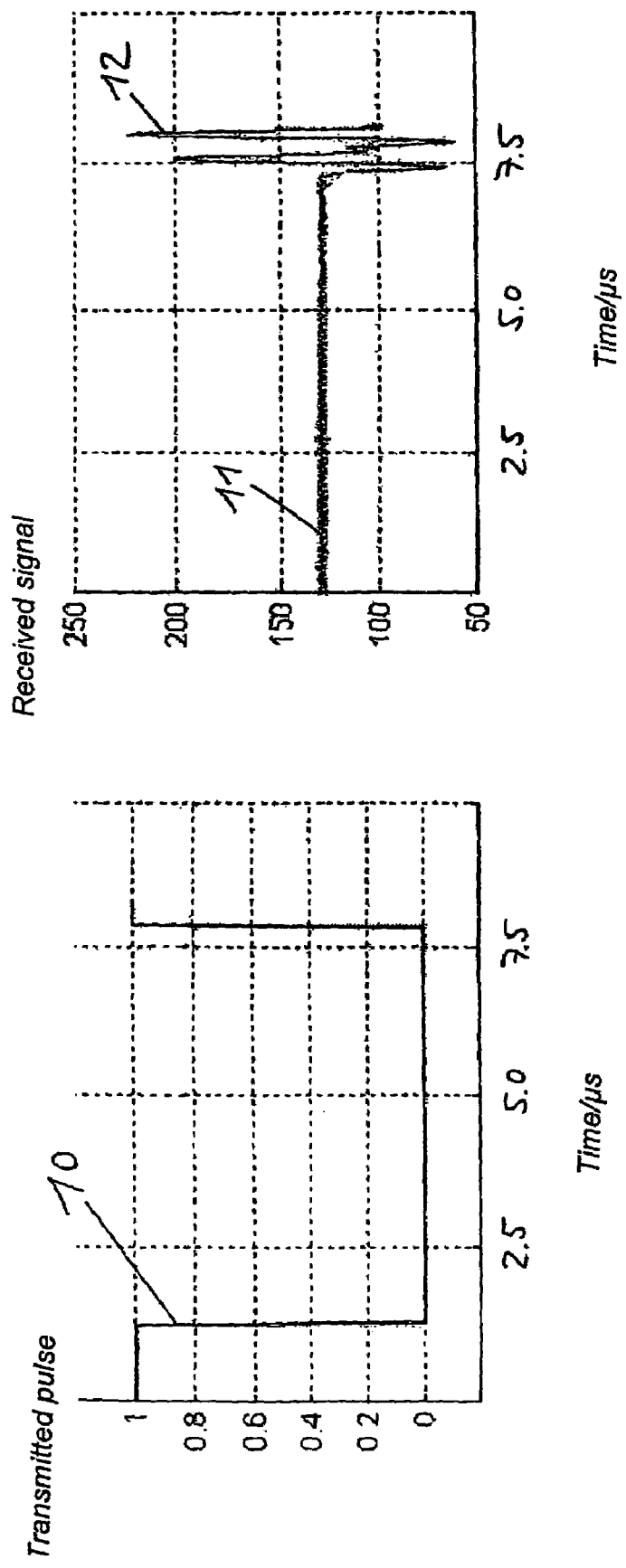
FIG. 2 the emitted signal and the received signal as a function of time.
Figure 3:
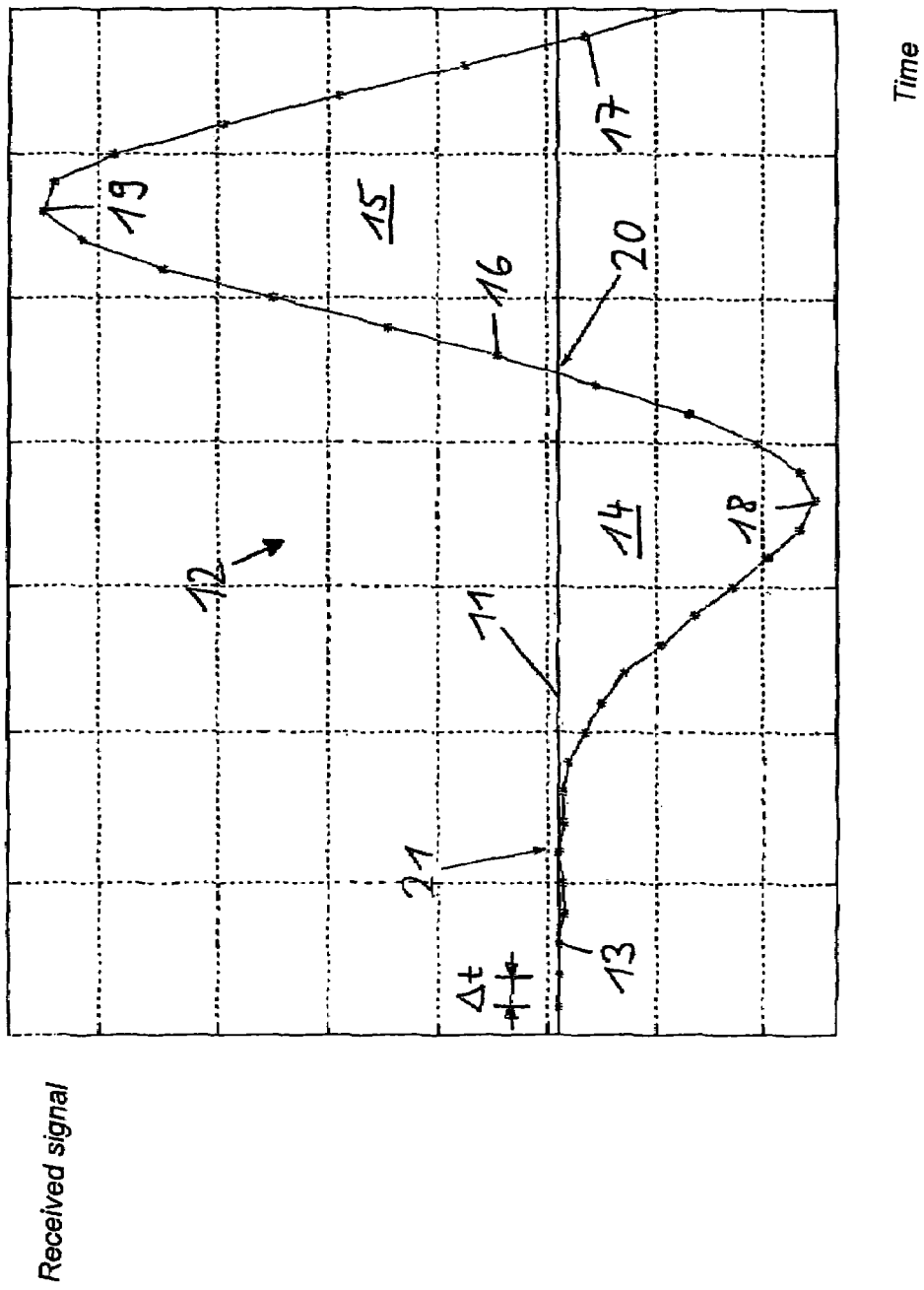
FIG. 3 an enlarged detail of the received signal-time diagram from FIG. 2.

The oscillator-like received signal 12 of FIG. 2 is shown on an enlarged scale in FIG. 3, which shows the individual signal values 13 which are sampled by the analyzer unit 6 at regular intervals t and stored as the value of an A/D converter connected to the signal line 5. The sampling rate, which is predetermined by an oscillator 7, designed as a temperature-compensated quartz oscillator, typically amounts to f=80 MHz, i.e., $\Delta t=1/f$ 12.5 ns. To increase the signal-to-noise ratio, the received signal may be smoothed, i.e., filtered, through sliding averaging.

To recognize a oscillator-like received signal 12 caused by the step-like signal 10 emitted, the stored signal values 13 are checked by a selection criterion. To do so at least one half-period 14 of the received signal is sampled according to this invention, this half-period extending to the signal value 16 in FIG. 3. It is also especially advantageous to detect the subsequent half-period 15 up to the signal value 17.

First, the analyzer unit 6 determines the resting level 11. To do so, progressive averaging may be used up to a termination criterion. For example, if the level falls below a predetermined value or if the level repeatedly falls below the previously determined resting level, this may indicate the start of the half-period 14 and the end of averaging for the resting level 11. If this event occurs, the analyzer unit 6 will integrate the area enclosed between the resting level 11 and the signal values 13 during the half-period 14. The end of the integration is recognized by the fact that the signal value 16 exceeds the resting level 11. In general, in integration in the sense of the selection criterion, it is sufficient to determine the enclosed area as the sum of the signal values of the half-period reduced by the resting level. Multiplication by the constant sampling period $\Delta t$ yields only a proposal result. However, if necessary, interpolated curves, in particular straight lines between the signal values 13 may be used to increase accuracy. However, this is associated with a considerable increase in computation complexity.

In addition, the analyzer unit determines the number of signal values including the half-period 14 and thus the duration of the half-period 14 as well as the extreme value 18 of the half-period 14. Reference values are stored in the analyzer unit 6 for all these variables, so that the measured values can be compared with the reference values. If the comparison ends positively with respect to the selection criterion, then the oscillator-like received signal 12 is recognized as a signal to be used for a measurement of the signal transit time or the change in the signal transit time. Otherwise the analyzer unit 6 discards this measurement cycle.

It should be pointed out that, based on the duration of the half-period 14, it must be within precisely defined limits because of the resonance response of the ultrasonic receiver 3, which is usually designed as a piezoelectric crystal and may also be predetermined precisely by its geometry—regardless of the actual transit time of the signal. Therefore, this selection criterion constitutes a very good discriminating criterion.

It is also conceivable for just individual selection criteria of those selection criteria mentioned here to be used in the analyzer unit 6. In practice, it has proven successful to combine the analysis of the extreme value and the duration of the half-period.

Appropriate analysis of the oscillator-like received signal 12 even during the subsequent half-period 15 up to the signal value 17 is especially advantageous. In addition to the area of the half-period 15, the extreme value 19 or the duration of the half-period 15, the relationships below the individual parameters, such as the ratio of the extreme values 18 and 19, which are reduced by the resting level, or the areas of the half-periods 14 and 15, may also be subjected to a selection criterion. In this way the reliability of selection of a received signal to be assigned to an emitted step-like signal can be increased progressively.

After a positive check of the received signal, the analyzer unit 6 determines the signal transit time or the change in signal transit time. To do so, the analyzer unit 6 determines an interpolated or extrapolated point of contact of the oscillator-like received signal 12 with the resting level 11 in the received signal-time diagram. Very accurate results can be achieved by determining the interpolated point of contact 20 between the first and second half-periods 14 and 15. Since a received signal for which the check with the selection criterion has turned out positive will have a sufficiently steep slope here, this point of contact 20 can be determined with a high precision by interpolation with the help of a straight line running through the two adjacent signal values. It is also possible to use other curve forms and other adjacent signal values for the interpolation. Those skilled in the art will be familiar with adequate means and methods to accomplish this.

The analyzer unit determines a value for the signal transit time from the distance in time between the emitted step-like signal 10 and the time coordinate of the point of contact 20. However, this is not the absolute signal time which instead is marked by the contact point 21 at the start of the first half-period 14. Determination of the contact point 21 by a similar interpolation procedure permits a determination of the absolute signal transit time. Since the slope is not as steep at this point, however, the value thus determined does not in general achieve the level of accuracy with which the contact point 20 can be determined. Here again, different criteria must be used here for selection of the signal values 13 to be taken into account because at the beginning of the half-period 14 there is not absolutely accurately one signal value above the resting level 11 and exactly one adjacent signal value below the resting level 11. In this case, it may be advisable to determine the contact point 21 by extrapolation of the curve through the first signal values 13 of the first half-period 14, in which case straight lines or other functions may be used, depending on the curve form.

The possibility of extrapolation of course also exists for other contact points in addition to contact point 20. Here again, however, the interpolation method will generally be preferred.

However, the interval in time between the contact points 20 and 21 is constant regardless of the signal transit time because of the resonance behavior of the ultrasonic receiver 3. In other words, this means that a change in the signal transit time due to a change in the composition of the blood in the region 31 of the line 1 between two points in time $t_1$, and $t_2$ has the same effect at both points. A corresponding change in the signal transit time can thus be determined with a high precision with the help of contact point 20. Although the time interval of the signal values 13 is $\Delta t=12.5$ ns, it is possible to achieve a time resolution in the subnanosecond range with the inventive method. Determination of the time coordinate of contact point 21 for the absolute transit time measurement at least permits a definite increase in accuracy.

Finally, under very constant test conditions, the absolute signal transit time can also be determined by determining the contact point 20 and subtracting the duration of the half-period 14, which is stored as a previously known value for these test conditions in analyzer unit 6.

With the help of the signal transit time thus determined or the change in the signal transit time, the analyzer unit can determine the composition of the medium flowing through line 1, namely in this case the blood-water content of the blood flowing through the line, on the basis of the information stored in the analyzer unit. It may also be sufficient to have a relative value which indicates a change in the blood-water content or the blood density and thus the blood volume in relation to an initial value at the start of the measurements. The sensor may be arranged on the extracorporeal circulation of a hemodialyzer machine to permit a determination of the change in the blood volume during a hemodialysis treatment.

At the same time, the analyzer unit 6 may use the transit time measurement to discriminate the medium flowing through the line 1. An extracorporeal circulation is prefilled with isotonic saline solution at the start of a hemodialysis treatment and is rinsed at the end of the treatment. Since the transit times in blood and in saline solution are fundamentally different, the analyzer unit 6 can differentiate the presence of one liquid or the other in line 1, which can be used to monitor the status or control the hemodialysis machine. Expediently in this case the analyzer unit 6 is part of the analyzer and/or control unit which is provided in hemodialysis machines anyway.

Furthermore, the analyzer unit 6 can analyze the areas of the half-periods 14 and/or 15 thus determined as a measure of the signal attenuation. In this way, the inventive device may also be used as an air detection sensor because even minor inclusions in the form of air bubbles in the blood flowing through line 1 can result in a reduction in the signal at the receiver 3. If there is only air in the line 1, this effect is especially pronounced in addition to the change in the transit time. In this particularly advantageous embodiment, the analyzer unit 6 is suitable for delivering appropriate alarm signals to the hemodialysis machine so that an infusion containing air, which would be dangerous for the patient, can be suppressed.

This invention provides a method and a device with which a reliable measurement with a high time resolution of signal transit times or changes in signal transit times is made possible despite the simple measurement components. This invention may be used for all medical media which pass through a measurement zone between a transmitter and a receiver, whereby the transit time of a step-like signal that is emitted is influenced by the medium. This invention is used in particular to determine the composition of blood in an extracorporeal blood circulation during a blood treatment such as hemodialysis in which it is desirable to observe the changes in blood volume and to prevent adverse side effects. At the same time, the inventive sensor may be used as an air detection sensor.

The invention being thus described, it will be apparent that the same may be varied in many ways. Such variations are not to be regarded as a departure from the spirit and scope of the invention, and all such modifications as would be recognized by one skilled in the art are intended to be included within the scope of the following claims.

What is claimed is:

1. A method of measuring a signal transit time in a medical liquid required by a signal to pass through a measurement zone from an ultrasonic transmitter (2) to an ultrasonic receiver (3), in which a line carrying the medical liquid is arranged in the measurement zone, comprising emitting a step-like signal (10) with the ultrasonic transmitter (2) such that the step-like signal (10) passes through the measurement zone, resulting in an oscillation-like received signal (12) oscillating about a resting level (11) on the ultrasonic receiver (3), the received signal being sampled at regular intervals $\Delta t$ and detected, checking the oscillator-like received signal (12) on the basis of a selection criterion at least during a half-period (14, 15) to determine whether the oscillator-like received signal (12) is the received signal produced by the step-like signal (10), and when the result of this check is positive, determining the signal transit time or the change in the signal transit time with an interpolated or extrapolated contact point (20, 21) of the oscillator-like received signal (12) with the resting level (11) in a received signal-time diagram.

2. The method according to claim 1, wherein for determining the signal transit time, the point used as the interpolated or extrapolated contact point is the point (21) in the received signal-time diagram at which the oscillator-like received signal (12) at the beginning of the first half-period (14) differs from the resting level (11).

3. The method according to claim 1, wherein for determining the change in signal transit time, the point (20) in the received signal-time diagram at which the oscillator-like received signal (12) intersects the resting level (11) after the first half-period (14) is determined as the interpolated or extrapolated contact point.

4. The method according claim 1, wherein an area enclosed between the oscillator-like received signal (12) and the resting level (11) is determined during the half-period (14).

5. The method according to claim 4, wherein the area determined is compared with a reference value as the selection criterion.

6. The method according to claim 4, wherein the subsequent half-period (15) is sampled and detected, and the area enclosed between the oscillator-like received signal (12) and the resting level (11) is determined during the subsequent half-period (15).

7. The method according to claim 6, wherein the area enclosed between the oscillator-like received signal (12) and the resting level (11) is compared with a reference value as the selection criterion during a subsequent half-period (15).

8. The method according to claim 1, wherein an extreme value (18) of the oscillator-like received signal (12) is determined during the half-period (14) and is compared with a reference value.

9. The method according to claim 8, wherein the subsequent half-period (15) is sampled and detected and an extreme value (19) of the oscillator-like received signal (12) is determined during the subsequent half-period (15) and compared with a reference value.

10. The method according to claim 1, wherein the duration of one or more half-periods (14, 15) of the oscillator-like received signal (12) is determined as the selection criterion and is compared with a reference value.

11. The method according to claim 1, wherein the resting level (11) is determined as the average of received signal samples (13) preceding the half-period (14).

12. The method according to claim 4, wherein the area determined is analyzed as a measure of the attenuation of the signal.

13. The method according to claim 1, wherein the medical liquid is blood, dialysis liquid or an infusion liquid.

14. A device for use of the method according to claim 1, comprising
   an ultrasonic transmitter (2) for emitting the step-like signal (10),
   an ultrasonic receiver (3) which is separated from the ultrasonic transmitter (2) by the measurement zone for delivering a received signal (12) which oscillates about a resting level (11) as the response to the step-like (10) signal passing through the measurement zone,
   a line (1) arranged in the measurement zone carrying a medical liquid,
   an analyzer unit (6) that is connected to the ultrasonic transmitter (2) and the ultrasonic receiver (3),
   the analyzer unit (6) receiving synchronized signals for sending the transmission signal and having a sampling device for sampling and storing the oscillator-like received signal (12) at regular intervals $\Delta t$,
   the analyzer unit (6) being configured for checking on the oscillator-like received signal (12) on the basis of a selection criterion at least during a half-period (14, 15) to determine whether the signal is the received signal caused by the step-like signal (10), and
   if the result of the test is positive, for determining the signal transit time or the change in the signal transit time of an interpolated or extrapolated contact point (20, 21) of the oscillator-like received signal (12) with a resting level (11) in a received signal-time diagram.

15. The device according to claim 14, wherein the analyzer unit (6) is configured for analyzing at least one of the signal transit time and the change in signal transit time as a measure of at least one of the composition and the change in composition of the medical liquid on the basis of stored information.

16. The device according to claim 14, wherein the medical liquid is blood, dialysis liquid or an infusion liquid.

17. The device according to claim 16, wherein the device is a blood volume sensor.

18. The device according to claim 17, wherein the device is the blood volume sensor and an air detection sensor.

* * * * *